United States Patent
Hirao et al.

(10) Patent No.: US 8,183,386 B2
(45) Date of Patent: May 22, 2012

(54) PHENYLNAPHTHYLIMIDAZOLE COMPOUND AND USAGE OF THE SAME

(75) Inventors: Hirohiko Hirao, Kagawa (JP);
Yoshimasa Kikukawa, Kagawa (JP);
Takayuki Murai, Kagawa (JP)

(73) Assignee: Shikoku Chemicals Corporation, Kagawa (JP)

( * ) Notice: Subject to any disclaimer, the term of this patent is extended or adjusted under 35 U.S.C. 154(b) by 761 days.

(21) Appl. No.: 11/629,179

(22) PCT Filed: Jun. 8, 2005

(86) PCT No.: PCT/JP2005/010898
§ 371 (c)(1),
(2), (4) Date: Dec. 11, 2006

(87) PCT Pub. No.: WO2005/121101
PCT Pub. Date: Dec. 22, 2005

(65) Prior Publication Data
US 2007/0246134 A1    Oct. 25, 2007

(30) Foreign Application Priority Data
Jun. 10, 2004   (JP) ................... 2004-173150
Jul. 27, 2004   (JP) ................... 2004-218230
Apr. 27, 2005   (JP) ................... 2005-128938

(51) Int. Cl.
*C07D 233/56*     (2006.01)
*C23C 22/05*     (2006.01)
(52) U.S. Cl. .................... 548/343.5; 148/269
(58) Field of Classification Search .............. 548/343.5; 148/269
See application file for complete search history.

(56) References Cited

U.S. PATENT DOCUMENTS

| 3,205,083 | A | * | 9/1965 | Green ........................... 252/588 |
| 5,498,301 | A | * | 3/1996 | Hirao et al. ................... 148/269 |
| 6,515,133 | B1 | * | 2/2003 | Thurkauf et al. .......... 546/274.1 |

FOREIGN PATENT DOCUMENTS

| EP | 0 627 499 | 12/1994 |
| JP | 42-1546 B | 1/1964 |
| JP | 08-183776 A2 | 7/1996 |
| JP | 10-280162 A | 10/1998 |
| JP | 2002-515400 A | 5/2002 |
| JP | 2004-244390 A | 9/2004 |
| JP | 2005-68530 A | 3/2005 |
| WO | 99/01128 A | 1/1999 |
| WO | 99/01128 A1 | 1/1999 |
| WO | WO 2002/083111 | * 10/2002 |

OTHER PUBLICATIONS

Murai et al. (CAPLUS Abstract of JP 2004-244390 A, published Sep. 2, 2004) and machine translation of the original document.*
Silverman, R. B. (The Org. Chem. of Drug Design and Drug Action, Academic Press, Inc.: San Diego, 1992, pp. 4-51).*
Japanese Office Action dated Jun. 23, 2008.
Database WPI Section Ch, Week 200462 Derwent Publications Ltd., London, GB; Class A60, AN 2004-637763 XP002342367 & JP 2004 244390 A (Shikoku Kasei Kogyo KK) Sep. 2, 2004.
Hideaki Yamaguchi et al, "Agent for protection of metal surface of printed circuit boards and manufacture thereof", XP002342365, Database Caplus 'Online!, Chemical Abstracts Service, Columbus, OH & JP 08 183776 A2 (Jul. 16, 1996).
Notification of Reasons for Refusal issued Oct. 25, 2010 in counterpart Japanese Application No. 2005-128938.
Communication dated Oct. 20, 2011, issued by the Indian Patent Office in corresponding Indian Patent Application No. 7443/DELNP/2006.
RN 104000-86-4 Registry ED Entered STN: Aug. 30, 1986 CN 1H-Imidazole, 5-(5-bromo-6-methoxy-2-naphthalenyl)-4-methyl-2-(4-nitrophenyl)- (CA Index Name).
RN 104000-87-5 Registry ED Entered STN: Aug. 30, 1986 CN 1H-Imidazole, 5-(5-bromo-6-methoxy-2-naphthalenyl)-4-methyl-2-(2-nitropheny1)-(CA Index Name).

* cited by examiner

*Primary Examiner* — Robert Havlin
(74) *Attorney, Agent, or Firm* — Sughrue Mion, PLLC

(57) ABSTRACT

A surface treating agent containing a novel phenylnaphthylimidazole compound represented by the following formula is brought into contact with the surface of copper or a copper alloy.

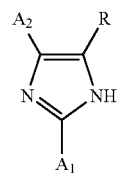

In the formula, when $A_1$ is a phenyl group, then $A_2$ represents a 1-naphthyl group or a 2-naphthyl group, and when $A_1$ is a 1-naphthyl group or a 2-naphthyl group, then $A_2$ represents a phenyl group; and R represents a hydrogen atom or a methyl group.

15 Claims, No Drawings

PHENYLNAPHTHYLIMIDAZOLE COMPOUND AND USAGE OF THE SAME

FIELD OF THE INVENTION

The present invention relates to a novel phenylnaphthylimidazole compound represented by the following formula (I); a surface treating agent which is used during soldering electronic parts or the like to copper or a copper alloy of a printed wiring board; a surface treatment method of copper or a copper alloy; a printed wiring board; and a soldering method.

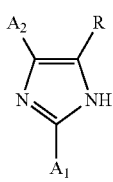
(I)

In the formula, when $A_1$ is a phenyl group, then $A_2$ represents a 1-naphthyl group or a 2-naphthyl group, and when $A_1$ is a 1-naphthyl group or a 2-naphthyl group, then $A_2$ represents a phenyl group; and R represents a hydrogen atom or a methyl group.

BACKGROUND OF THE INVENTION

In recent years, surface mount technology with high density has been widely adopted. Such surface mount technology are classified, among others, into double-sided surface mount technology in which chip type parts are joined with use of solder paste, and hybrid mount technology which is a combination of surface mount technology of chip type parts using solder paste and through-hole mount technology of discrete parts. In either mount process, a printed wiring board is subjected to two or more soldering steps, and thus it is exposed to high temperatures resulting in a severe thermal history.

Oxide film formation is accelerated by heating the surface of copper or copper alloys constituting the circuit part of a printed wiring board, and thus the surface of the circuit part cannot maintain good solderability.

In order to protect the copper circuit part of the printed wiring board from air oxidation, a chemical layer is generally formed on the surface of the circuit part using a surface treating agent. It is necessary, however, that good solderability be maintained by preventing the chemical layer from degenerating (i.e., being degraded) to protect the copper circuit part even after the copper circuit part has a thermal history of multiple cycles.

Tin-lead alloy eutectic solders have been conventionally used for mounting electronic parts to a printed wiring board, etc. In recent years, however, concerns have developed that the lead contained in the solder alloy adversely affects the human body, and thus the use of lead-free solder is desired.

Accordingly, various lead-free solders are being considered. For example, lead-free solders have been suggested in which one or more metals, such as silver, zinc, bismuth, indium, antimony, copper, etc., are added to a base metal of tin.

The conventionally used tin-lead eutectic solder is excellent in wettability on the surface of substrate, particularly copper, and thus strongly adheres to copper, resulting in high reliability. In contrast, lead-free solder is inferior to the conventionally used tin-lead solder in wettability on a copper surface, and thus exhibits poor solderability and low bonding strength due to voids and other bonding defects.

Therefore, when using lead-free solder, it is necessary to select a solder alloy with superior solderability and a flux which is suitable for use with lead-free solder. A surface treatment agent for use in preventing oxidation on the surface of copper or a copper alloy is also required to have functions for improving the wettability and solderability of the lead-free solder.

Many lead-free solders have a high melting point, and a soldering temperature that is about 20 to about 50° C. higher than that of the conventionally used tin-lead eutectic solder. Thus, surface treatment agent for use in the process of soldering with lead-free solder should have the characteristic of being able to form a chemical layer with excellent heat resistance.

As active ingredients of these surface treating agents, various imidazole compounds have been proposed. For example, Patent Document 1 disclose 2-alkylimidazole compounds such as 2-undecylimidazole; Patent Document 2 discloses 2-arylimidazole compounds such as 2-phenylimidazole and 2-phenyl-4-methylimidazole; Patent Document 3 discloses 2-alkyl-benzimidazole compounds such as 2-nonylbenzimidazole; and Patent Document 4 discloses 2-aralkylbenzimidazole compounds such as 2-(4-chlorophenylmethyl)benzimidazole, respectively.

However, in the case where a surface treating agent containing such an imidazole compound is used, the heat resistance of a chemical layer as formed on the copper surface was not satisfactory yet. Also, in soldering, the solder wettability is not sufficient so that good solderability cannot be obtained. In particular, in the case of performing soldering using a lead-free solder in place of the eutectic solder, it was difficult to put the foregoing surface treating agent into practical use.

[Patent Document 1] JP-B-46-17046
[Patent Document 2] JP-A-4-206681
[Patent Document 3] JP-A-5-25407
[Patent Document 4] JP-A-5-186888

SUMMARY OF THE INVENTION

In view of the foregoing circumstance, the invention has been made. An object of the invention is to provide a novel phenylnaphthylimidazole compound, and to provide a surface treating agent, which in mounting electronic parts or the like to a printed wiring board using an eutectic solder or a lead-free solder, forms a chemical layer having excellent heat resistance on the surface of copper or a copper alloy constituting a circuit part of a printed wiring board or the like and at the same time, improves the wettability to the solder and makes the solderability good and a surface treatment method.

Also, another object of the invention is to provide a printed wiring board resulting from bringing the surface of copper or a copper alloy constituting a copper circuit part into contact with the foregoing surface treating agent and to provide a soldering method by bringing the surface of copper or a copper alloy into contact with the foregoing surface treating agent and then performing soldering using an eutectic solder or a lead-free solder.

In order to solve the foregoing problems, the present inventors made extensive and intensive investigations. As a result, it has been found that by bringing a surface treating agent containing a novel phenylnaphthylimidazole compound represented by the foregoing formula (I) as an active ingredient into contact with the surface of copper or a copper alloy, the objects of the invention can be achieved, leading to accomplishment of the invention.

The surface treating agent containing a novel phenylnaphthylimidazole compound according to the invention is not only able to form a chemical layer having excellent heat resistance on the surface of copper or a copper alloy constituting a circuit part of a printed wiring board or the like but also able to greatly improve the wettability of an eutectic solder and a lead-free solder to the subject surface and make the solderability good.

Also, since the soldering method according to the invention makes it possible to use a solder not containing lead which is a harmful metal, it is useful from the viewpoint of environmental protection.

DETAILED DESCRIPTION OF THE INVENTION

Best modes for carrying out the invention will be described below.

The phenylnaphthylimidazole compound according to the invention includes:
2-phenyl-4-(1-naphthyl)imidazole,
2-phenyl-4-(2-naphthyl)imidazole,
2-phenyl-4-(1-naphthyl)-5-methylimidazole,
2-phenyl-4-(2-naphthyl)-5-methylimidazole,
2-(1-naphthyl)-4-phenylimidazole,
2-(2-naphthyl)-4-phenylimidazole,
2-(1-naphthyl)-4-phenyl-5-methylimidazole, and
2-(2-naphthyl)-4-phenyl-5-methylimidazole.

The phenylnaphthylimidazole compound according to the invention can be synthesized according to known methods. That is, among the phenylnaphthylimidazole compounds according to the invention, compounds classified into a 2-phenyl-4-naphthylimidazole compound in which the 2-position and 4-position of the imidazole ring thereof are substituted with a phenyl group and a naphthyl group, respectively, i.e., 2-phenyl-4-(1-naphthyl)imidazole, 2-phenyl-(4-(2-naphthyl)-imidazole, 2-phenyl-4-(1-naphthyl)-5-methylimidazole, and 2-phenyl-4-(2-naphthyl)-5-methylimidazole, can be, for example, synthesized by reacting a 2-halogenated naphthyl-alkylketone compound and a benzamidine compound under heating in an organic solvent in the presence of a dehydrohalogenating agent as shown in the following reaction scheme.

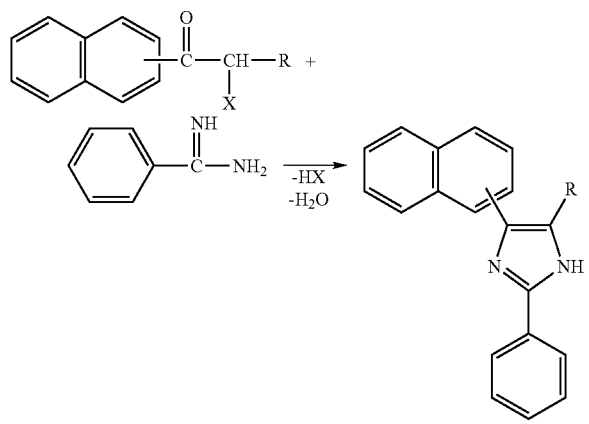

In the formulae, X may represent a chlorine atom, a bromine atom, or an iodine atom; and R may represent a hydrogen atom or a methyl group.

In the reaction as shown in the foregoing reaction scheme, the amount of the benzamidine compound to be used may be preferably in a proportion of from 0.8 to 1.5 times by mole, and more preferably from 0.9 to 1.1 times by moles based on the 2-halogenated naphthylalkylketone compound. The amount of the dehydrohalogenating agent to be used is preferably in a proportion of from 1 to 10 equivalent times based on the 2-halogenated naphthylalkylketone compound.

Examples of the foregoing 2-halogenated naphthylalkylketone compounds include ω-bromo-1-acetonaphthone, ω-bromo-2-acetonaphthone, 2-bromo-1'-propionaphthone, 2-bromo-2'-propionaphthone, ω-chloro-1-acetonaphthone, ω-iodo-1-acetonaphthone, 2-chloro-1'-propionaphthone, and 2-iodo-2'-propionaphthone.

Among these 2-halogenated naphthylalkylketone compounds, ω-bromo-2-acetonaphthone is available as a reagent. Moreover, regarding other compounds besides ω-bromo-2-acetonaphthone, those, for example, which are synthesized by halogenating a naphthylalkylkeone compound at the 2-position can be used. With respect to the halogenation at the 2-position, though chlorination at the 2-position and iodination at the 2-position are possible, bromination at the 2-position for reacting one mole of a naphthylalkylketone compound with one mole bromine is the simplest.

Among the naphthylalkylketone compounds, examples of the acetonaphthone compound include 1-acetonaphthone and 2-acetonaphthone, both of which are known and easily available.

Among the naphthylalkylketone compounds, examples of the propionaphthone compound include 1-propionaphthone and 2-propionaphthone. The 1-propionaphthone can be obtained, for example, by reacting naphthalene with a propionyl chloride.aluminum chloride complex using 1,2-dichloroethane or the like as a solvent (see Reference Example 1 as described later).

The 2-propionaphthone can be obtained, for example, by reacting 2-naphthonitrile with magnesium ethyl bromide or the like and hydrolyzing the reaction mixture under a strongly acidic condition (see Reference Example 2 as described later).

Examples of the benzamidine compound include benzamidine; organic acid salts of benzamidine such as benzamidine acetate; and inorganic acid salts of benzamidine such as benzamidine hydrochloride.

As the dehydrohalogenating agent, known compounds can be used without limitations. Examples of such a dehydrohalogenating agent include inorganic alkalis such as sodium hydroxide, potassium hydroxide, calcium hydroxide, sodium carbonate, potassium carbonate, sodium bicarbonate, and potassium bicarbonate; organic bases such as triethylamine and 1,8-diazabicyclo[5.4.0]-7-undecene (DBU); and metallic alkoxide compounds such as sodium methoxide and potassium t-butoxide.

As the reaction solvent, known compounds can be used without limitations so far as they can dissolve, for example, the 2-halogenated naphthylalkylketone compound and the benzamidine compound therein and do not participate in the reaction. Examples of suitable solvents include alcohols such as ethanol and isopropyl alcohol; hydrocarbons such as hexane and toluene; halogenated hydrocarbons such as chloroform and chlorobenzene; esters such as ethyl acetate; nitriles such as acetonitrile; ethers such as tetrahydrofuran and dioxane; amides such as dimethylformamide (DMF) and dimethylacetamide (DMAC); and besides, dimethyl sulfoxide (DMSO).

The reaction temperature is preferably from room temperature to the reflux temperature; and the reaction time is preferably from 1 to 10 hours. The reaction may be usually performed under the atmospheric pressure.

The 2-phenyl-4-naphthylimidazole compounds as formed under the foregoing reaction conditions can be taken out by, for example, the following isolation operation. That is, after completion of the reaction, a crude desired material can be obtained as a solid by, for example, adding a large amount of water to the obtained reaction mixture or a concentrate from which the solvent has been distilled off from the reaction mixture. This crude material can be purified by a recrystallization operation or the like.

Among the phenylnaphthylimidazole compounds according to the invention, compounds classified into a 2-naphthyl-4-phenylimidazole compound in which the 2-position and 4-position of the imidazole ring thereof are substituted with a naphthyl group and a phenyl group, respectively, with the 5-position being not substituted, i.e., 2-(1-naphthyl)-4-phenylimidazole and 2-(2-naphthyl)-4-phenylimidazole, can be, for example, synthesized by reacting a naphthaldehyde compound, 2-acetoxyacetophenone, ammonia, and copper(II) acetate under heating in a water-soluble organic solvent such as alcohols as shown in the following reaction scheme.

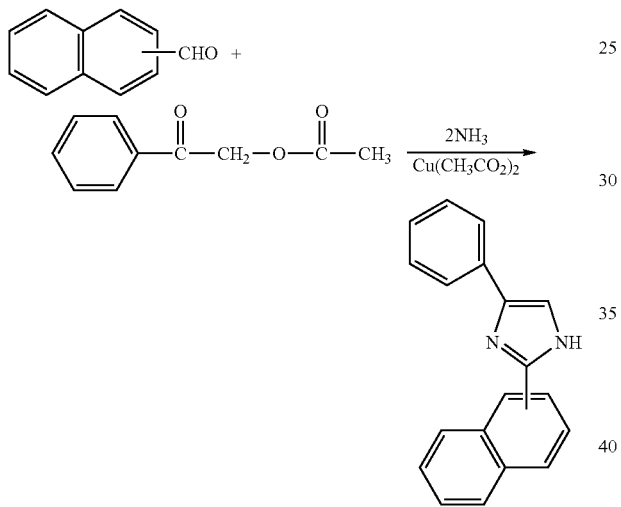

In the reaction as shown in the foregoing reaction scheme, the amount of the 2-acetoxyacetophenone to be used may be preferably in a proportion of from 0.8 to 1.5 times by mole, and more preferably from 0.9 to 1.1 times by mole based on the naphthaldehyde compound. The amount of ammonia to be used may be preferably in a proportion of from 10 to 50 times by mole, and more preferably from 20 to 30 times by mole based on the naphthaldehyde compound. The amount of copper(II) acetate to be used may be preferably in a proportion of from 1 to 5 times by mole, and more preferably from 2 to 3 times by mole based on the naphthaldehyde compound.

The 2-acetoxyacetophenone can be obtained by, for example, reacting 2-chloroacetophenone with potassium acetate (see Reference Example 3 as described later). Also, the naphthaldehyde compound includes 1-naphthaldehyde and 2-naphthaldehyde, and these compounds are known and easily available.

Examples of the reaction solvent include alcohols such as methanol, ethanol, propanol, and isopropanol, acetonitrile, and tetrahydrofuran.

The reaction temperature is preferably from 50 to 80° C.; and the reaction time is preferably from 1 to 10 hours. The reaction may be usually performed under the atmospheric pressure.

The 2-naphthyl-4-phenylimidazole compound as formed under the foregoing reaction conditions can be taken out by, for example, the following isolation operation. That is, after completion of the reaction, a precipitate is collected by filtration, and the deposit is suspended in methanol. Next, sodium hydrosulfide in an amount of from 0.5 to 0.8 times by mole based on the naphthaldehyde compound is added to this methanol suspension step by step until sodium hydrosulfide has been no longer consumed; deposited copper sulfide is filtered out; the methanol is distilled off in vacuo; and the residue is rinsed with water, whereby a crude desired material can be obtained as a solid. This crude material can be purified by a recrystallization operation or the like.

Among the phenylnaphthylimidazole compounds according to the invention, compounds classified into a 2-naphthyl-4-phenyl-5-methylimidazole compound in which the 2-position, 4-position and 5-position of the imidazole ring thereof are substituted with a naphthyl group, a phenyl group and a methyl group, respectively, i.e., 2-(1-naphthyl)-4-phenyl-5-methylimidazole and 2-(2-naphthyl)-4-phenyl-5-methylimidazole, can be, for example, synthesized by reacting a naphthaldehyde compound, 1-phenyl-1,2-propanedione, and ammonium acetate in acetic acid under heating as shown in the following reaction scheme.

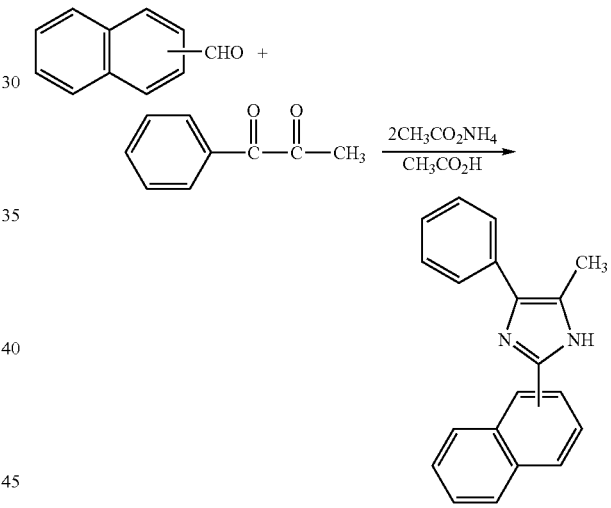

In the reaction as shown in the foregoing reaction scheme, the amount of the 1-phenyl-1,2-propanedione to be used may be preferably in a proportion of from 0.8 to 1.5 times by mole, and more preferably from 0.9 to 1.1 times by mole based on the naphthaldehyde compound. The amount of ammonium acetate to be used may be preferably in a proportion of from 2 to 10 times by mole, and more preferably from 4 to 6 times by mole based on the naphthaldehyde compound.

The naphthaldehyde compound which is used in this reaction includes 1-naphthaldehyde and 2-naphthaldehyde, and these compounds are the same as described previously.

The reaction temperature is preferably from 80° C. to the reflux temperature; and the reaction time is preferably from 1 to 10 hours. The reaction may be usually performed under the atmospheric pressure.

The 2-naphthyl-4-phenyl-5-methylimidazole compound as formed under the foregoing reaction conditions can be taken out by, for example, the following isolation operation. That is, after completion of the reaction, the reaction mixture or a residue obtained by distilling off the acetic acid from the reaction mixture and an alkaline agent (for example, sodium hydroxide, sodium carbonate, and ammonia) in an excessive amount against the acetic acid contained therein are dissolved in water and mixed, whereby a crude desired material can be precipitated. This crude material can be purified by a recrystallization operation or the like.

The phenylnaphthylimidazole compound may be dissolved in a suitable carrier, such as water or an organic solvent, to form the surface treating agent.

The phenylnaphthylimidazole compound may be contained, for example, in a proportion of from 0.01 to 10% by weight, and preferably from 0.1 to 5% by weight in the surface treating agent. When the content of the imidazole compound is less than 0.01% by weight, the film thickness of the chemical layer as formed on the surface of copper may be too thin so that the oxidation of the surface of copper cannot be prevented. On the other hand, when it exceeds 10% by weight, the imidazole compound in the surface treating agent may leave without being dissolved so that a uniform aqueous solution cannot be formed.

In dissolving the imidazole compound in water (forming an aqueous solution), an organic acid or an inorganic acid may be used as the acid, but a small amount of an organic solvent may be used simultaneously. Representative examples of the organic acid to be used include formic acid, acetic acid, propionic acid, butyric acid, glyoxylic acid, pyruvic acid, acetoacetic acid, levulinic acid, heptanoic acid, caprylic acid, capric acid, lauric acid, glycolic acid, glyceric acid, lactic acid, acrylic acid, methoxyacetic acid, ethoxyacetic acid, propoxyacetic acid, butoxyacetic acid, 2-(2-methoxyethoxy)acetic acid, 2-[2-(2-ethoxyethoxy)ethoxy]acetic acid, 2-{2-[2-(2-ethoxyethoxy)ethoxy]ethoxy}acetic acid, methoxypropionic acid, ethoxypropionic acid, propoxypropionic acid, butoxypropionic acid, benzoic acid, p-nitrobenzoic acid, p-toluenesulfonic acid, salicylic acid, picric acid, oxalic acid, succinic acid, maleic acid, fumaric acid, tartaric acid, and adipic acid; and examples of the inorganic acid include hydrochloric acid, phosphoric acid, sulfuric acid, and nitric acid.

Such an acid may be added in a proportion of from 0.1 to 50% by weight, and preferably from 1 to 30% by weight based on the aqueous solution.

Also, examples of the organic solvent include lower alcohols such as methanol, ethanol, and isopropanol, or acetone, N,N-dimethylformamide, and ethylene glycol and the like, which are freely miscible mixed with water.

To the surface treating agent of the invention, a metal salt may be added. In the case where a copper compound is used as the metal salt, it may be possible to hasten the formation rate of the chemical layer on the surface of copper or a copper alloy. Also, in the case where a zinc compound is used as the metal salt, it may be possible to further enhance the heat resistance of the chemical layer.

Representative examples of the copper compound include copper acetate, cuprous chloride, cupric chloride, cuprous bromide, cupric bromide, copper iodide, copper hydroxide, copper phosphate, copper sulfate, and copper nitrate; and representative examples of the zinc compound include zinc oxide, zinc formate, zinc acetate, zinc oxalate, zinc lactate, zinc citrate, zinc sulfate, zinc nitrate, and zinc phosphate. These metal salts may be used singly or in combinations of two or more kinds thereof. The metal salt may be added in a proportion of from 0.01 to 10% by weight, and preferably from 0.02 to 5% by weight in the surface treating agent.

In the case where such a copper compound or zinc compound is used, it may be desirable to stabilize the pH of the solution by adding a substance having a buffer action, such as ammonia, monoethanolamine, diethanolamine, and triethanolamine in addition to the organic acid or inorganic acid.

For the purpose of further enhancing the formation rate of the chemical layer and the heat resistance of the film, a halogen compound may be added in the surface treating agent according to the invention. Examples of the halogen compound include sodium fluoride, potassium fluoride, ammonium fluoride, sodium chloride, potassium chloride, ammonium chloride, sodium bromide, potassium bromide, ammonium bromide, sodium iodide, potassium iodide, and ammonium iodide. These halogen compounds may be used singly or in combinations of two or more kinds thereof. The halogen compound may be added in a proportion of from 0.001 to 1% by weight, and preferably from 0.01 to 0.1% by weight in the surface treating agent.

With respect to the conditions for treating the surface of copper or a copper alloy using the surface treating agent according to the invention, the liquid temperature of the surface treating agent may be, for example, from 10 to 70° C., and the contact time may be, for example, from 1 second to 10 minutes. Examples of the contact method include dipping, spraying, and coating methods.

Also, after performing the surface treatment according to the invention, it is possible to further enhance the heat resistance by forming a double structure on the chemical layer with a thermoplastic resin.

That is, after forming the chemical layer on the surface of copper or a copper alloy, a double structure of the chemical layer and a thermoplastic resin may be formed by dissolving a thermoplastic resin having excellent heat resistance, which may be composed, for example, of a rosin derivative (for example, rosin and rosin esters), a terpene resin derivative (for example, terpene resins and terpene phenol resins), a hydrocarbon resin (for example, aromatic hydrocarbon resins and aliphatic hydrocarbon resins), or a mixture thereof, in a solvent (for example, toluene, ethyl acetate, and isopropyl alcohol) and uniformly coating the solution in a thickness of, for example, from 1 to 30 μm on the chemical layer using, for example, a roll coater or the like.

Examples of the solder which is suitable for carrying out the invention include not only generally used tin-lead alloy eutectic solders but also lead-free solders such Sn—Ag—Cu based, Sn—Ag—Bi based, Sn—Bi based, Sn—Ag—Bi—In based, Sn—Zn based, and Sn—Cu based solders.

Also, the soldering method of the invention can be adapted to the flow soldering method and reflow soldering method.

Flow soldering comprises moving a printed wiring board over a molten liquid-state solder in a solder bath for soldering junctions between electronic parts and the printed wiring board.

In contrast, reflow soldering comprises printing in advance a paste cream solder on the printed wiring board according to a circuit pattern, mounting electronic parts thereon, and heating the whole printed wiring board to melt the solder to complete the soldering.

EXAMPLES

Synthesis examples of the phenylnaphthylimidazole compounds of the invention will be specifically described below with reference to Examples 1 to 8, but it should not be construed that the invention is limited thereto. Incidentally, principal raw materials which were used for the syntheses of the phenylnaphthylimidazole compounds are as follows.

(Raw Materials)

Benzamidine hydrochloride (a reagent manufactured by Tokyo Kasei Kogyo Co., Ltd.)

ω-Bromo-1-acetonaphthone (prepared by the method as described in JP-A-9-286755)

ω-Bromo-2-acetonaphthone (a reagent manufactured by Tokyo Kasei Kogyo Co., Ltd.)

1-Propionaphthone (prepared by the method as described in Reference Example 1)

2-Propionaphthone (prepared by the method as described in Reference Example 2)

2-Acetoxyacetonaphthone (prepared by the method as described in Reference Example 3)

1-Naphthaldehyde (a reagent manufactured by Tokyo Kasei Kogyo Co., Ltd.)

2-Naphthaldehyde (a reagent manufactured by Tokyo Kasei Kogyo Co., Ltd.)

1-Phenyl-1,2-propanedione (a reagent manufactured by Tokyo Kasei Kogyo Co., Ltd.)

Reference Example 1

Preparation of 1-propionaphthone 143.7 g (1.08 mol) of aluminum chloride was added by portions to a solution consisting of 92.6 g (1.0 mol) of propionyl chloride and 320 mL of 1,2-dichloroethane step by step at 5 to 10° C., and after completion of addition, the temperature was elevated to room temperature to prepare a 1,2-dichloroethane solution of a propionyl chloride.aluminum chloride complex.

The foregoing 1,2-dichloroethane solution of a propionyl chloride.aluminum chloride complex was added dropwise to a solution consisting of 128.2 g (1.0 mol) of naphthalene and 300 mL of 1,2-dichloroethane at 35 to 40° C. over one hour. After completion of addition, the resulting mixed liquid was heated at 45 to 50° C. for 2 hours and after cooling to room temperature, was poured into, ice water. 200 mL of concentrated hydrochloric acid was further added thereto, and the mixture was stirred and mixed. The product as formed in this reaction mixture was extracted with chloroform together with 1,2-dichloroethane, dried over magnesium sulfate, and concentrated in vacuo. A concentrated liquid was distilled in vacuo to obtain 145.3 g (yield: 79%, boiling point: 139 to 142° C./4 mmHg) of 1-propionaphthone as a pale yellow oil.

Reference Example 2

Preparation of 2-propionaphthone 50.8 g (0.33 mol) of 2-naphthonitrile was gradually added to a solution consisting of 164 g (0.5 mol) of a diethyl ether solution of magnesium ethyl bromide having a concentration of 3M and 120 ml of dry benzene, and after cease of heat generation, heating was started. About 100 mL of a distillate composed mainly of the diethyl ether was distilled off, 100 mL of benzene was added, and the mixture was heated under reflux for 3 hours. After completion of heating, the reaction mixture was cooled to room temperature; a solution consisting of 35 g (0.654 mol) of ammonium chloride and 140 mL of water was added; the aqueous layer was removed; 600 mL of 6N hydrochloric acid was added; and the mixture was heated under reflux for 4 hours. After cooling, the aqueous layer was removed; and the organic layer was washed with water, dried over sodium sulfate, and then evaporated to dryness in vacuo to obtain 57.3 g (yield: 94.2%) of 2-propionaphthone as a dark yellow solid.

Reference Example 3

Preparation of 2-acetoxyacetophenone 78.5 g (0.80 mol) of potassium acetate, 5.0 g (0.08 mol) of acetic acid, and 123.7 g (0.80 mol) of 2-chloroacetophenone were heated under reflux in 500 mL of ethanol for 6 hours. After completion of heating, the reaction mixture was cooled to room temperature, deposited potassium chloride was filtered off, and the ethanol was distilled off in vacuo to obtain a pale brown oily material. This oily material was poured into one litter of water, and a precipitated solid was collected by filtration and recrystallized from methanol to obtain 113.1 g (yield: 79.3%) of 2-acetoxyacetophenone as a pale yellow solid.

Example 1

Synthesis of 2-phenyl-4-(1-naphthyl)imidazole

A suspension consisting of 31.3 g (0.20 mol) of benzamidine hydrochloride, 10.8 g (0.20 mol) of sodium methylate, and 150 mL of tetrahydrofuran was heated under reflux for one hour. After cooling to 25° C., a solution consisting of 49.8 g (0.2 mol) of ω-bromo-1-acetonaphthone and 100 mL of tetrahydrofuran was added dropwise such that the internal temperature did not exceed 30° C. After completion of addition, 10.8 g (0.20 mol) of sodium methylate was added, and the mixture was heated under reflux for one hour. Next, the reaction mixture was cooled to room temperature, insoluble matters were filtered off, and the filtrate was evaporated to dryness in vacuo. The residual solid was successively washed with water and acetonitrile and then dried to obtain a crude crystal as a desired material. This crude crystal was recrystallized from acetonitrile to obtain 18.0 g (yield: 33.3%) of a grayish blue crystal.

The melting point, Rf value of thin layer chromatography, and NMR and mass spectral data of the resulting crystal are as follows.

m.p.: 167 to 169° C.

TLC (silica gel, chloroform/ethyl acetate=9/1), Rf=0.90

NMR (CD$_3$OD): δ 7.3 to 8.4 (m)

MS m/z (%): 270 (M+, 100), 167 (56), 139 (20), 117 (5), 104 (7), 89 (6)

From these spectral data, the resulting compound was identified as 2-phenyl-4-(1-naphthyl)imidazole represented by the following formula.

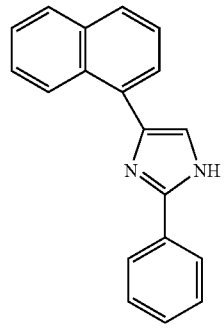

Example 2

Synthesis of 2-phenyl-4-(2-naphthyl)imidazole

A suspension consisting of 31.3 g (0.20 mol) of benzamidine hydrochloride, 10.8 g (0.20 mol) of sodium methylate, and 150 mL of tetrahydrofuran was heated under reflux for one hour. After cooling to 20° C., a solution consisting of 49.8 g (0.2 mol) of ω-bromo-2-acetonaphthone and 100 mL of tetrahydrofuran was added dropwise such that the internal temperature did not exceed 30° C. After completion of addition, 10.8 g (0.20 mol) of sodium methylate was added, and the mixture was heated under reflux for one hour. Next, the reaction mixture was cooled to room temperature, insoluble matters were filtered off, and the filtrate was evaporated to dryness in vacuo. The residual solid was successively washed with water and toluene and then dried to obtain a crude crystal as a desired material. This crude crystal was recrystallized from acetonitrile to obtain 32.8 g (yield: 60.7%) of a colorless crystal.

The melting point, Rf value of thin layer chromatography, and NMR and mass spectral data of the resulting crystal are as follows.

m.p.: 230 to 233° C.
TLC (silica gel, chloroform/ethyl acetate=9/1), Rf=0.33
NMR (CD$_3$OD): δ 7.4 to 8.3 (m)
MS m/z (%): 270 (M+, 100), 243 (5), 166 (11), 139 (21), 117 (10), 86 (6)

From these spectral data, the resulting compound was identified as 2-phenyl-4-(2-naphthyl)imidazole represented by the following formula.

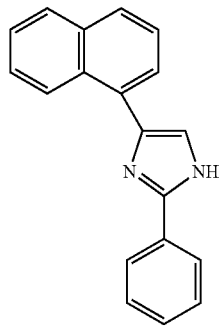

Example 3

Synthesis of
2-phenyl-4-(1-naphthyl)-5-methylimidazole 53.3 g (0.334 mol) of bromine was added dropwise to a solution consisting of 61.1 g (0.332 mol) of 1-propionaphthone and 180 mL of ethanol at 50 to 55° C. After completion of addition, the ethanol was distilled off in vacuo, and the resulting concentrate was dissolved in 130 mL of toluene, washed with a mixed aqueous solution of sodium bicarbonate and sodium chloride (150 mL×two times), and then dried over sodium sulfate to obtain a toluene solution of 2-bromo-1'-propionaphthone.

A suspension consisting of 50.1 g (0.32 mol) of benzamidine hydrochloride, 133 g (0.96 mol) of potassium carbonate, and 250 mL of tetrahydrofuran was heated under reflux for one hour, and the foregoing toluene solution of 2-bromo-1'-propionaphthone was added dropwise over 50 minutes. After completion of addition, heated under reflux for 2 hours. Next, the reaction mixture was concentrated in vacuo, the resulting concentrate was diluted with 200 mL of toluene, and the solution was poured into 600 mL of water. The mixture was stirred to precipitate a solid. This solid was collected by filtration, successively washed with toluene and water, and then dried to obtain a crude crystal as a desired material. This crude crystal was recrystallized from DMF to obtain 48.1 g (yield: 52.9%) of a white powder.

The melting point, Rf value of thin layer chromatography, and NMR and mass spectral data of the resulting powder are as follows.

m.p.: 280 to 282° C.
TLC (silica gel, acetone); Rf=0.65
NMR (d$_6$-DMSO): δ 2.27 (s, 3H), 7.38 to 8.27 (m, 12H)
MS m/z (%): 284 (M+, 100), 269 (1), 215 (4), 180 (23), 166 (4), 153 (17), 139 (10), 127 (7), 104 (10), 89 (6), 77 (10), 62 (6)

From these spectral data, the resulting compound was identified as 2-phenyl-4-(1-naphthyl)-5-methylimidazole represented by the following formula.

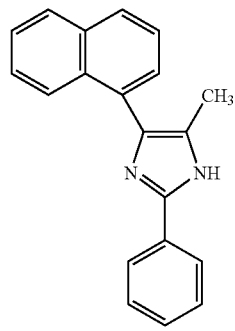

Example 4

Synthesis of
2-phenyl-4-(2-naphthyl)-5-methylimidazole 46.0 g (0.288 mol) of bromine was added dropwise to a solution consisting of 55.8 g (0.303 mol) of 2-propionaphthone and 250 mL of ethanol at 50 to 55° C. After completion of addition, the ethanol was distilled off in vacuo; and the resulting concentrate was dissolved in 130 mL of toluene, washed with a mixed aqueous solution of sodium bicarbonate and sodium chloride (200 mL×two times), and then dried over sodium sulfate to obtain a toluene solution of 2-bromo-2'-propionaphthone.

A suspension consisting of 45.1 g (0.288 mol) of benzamidine hydrochloride, 119.4 g (0.864 mol) of potassium carbonate, and 240 mL of tetrahydrofuran was heated under reflux for one hour, and the foregoing toluene solution of 2-bromo-2'-propionaphthone was added dropwise over 40 minutes. After completion of addition, heating under reflux was continued for 2 hours. Next, the reaction mixture was concentrated in vacuo, the resulting concentrate was diluted with 200 mL of toluene, and the solution was poured into 600 mL of water. The mixture was stirred to precipitate a solid. This solid was collected by filtration, successively washed with toluene and water, and then dried to obtain a crude crystal as a desired material. This crude crystal was recrystallized from acetonitrile to obtain 55.0 g (yield: 67.2%) of a white powder.

The melting point, Rf value of thin layer chromatography, and NMR and mass spectral data of the resulting powder are as follows.

m.p.: 215 to 218° C.
TLC (silica gel, acetone), Rf=0.69
NMR (CDCl$_3$): δ 2.56 (s, 3H), 7.34 to 8.03 (m, 12H)

MS m/z (%): 284 (M+, 100), 243 (1), 215 (2), 180 (14), 153 (12), 139 (9), 127 (4), 104 (7), 89 (5), 77 (7), 63 (5)

From these spectral data, the resulting compound was identified as 2-phenyl-4-(2-naphthyl)-5-methylimidazole represented by the following formula.

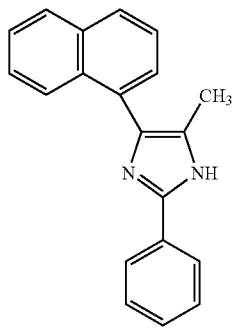

Example 5

Synthesis of 2-(1-naphthyl)-4-phenylimidazole

A solution consisting of 70.3 g (0.352 mol) of copper(II) acetate monohydrate and 220 g (3.2 mol) of 25% ammonia water was added dropwise to a solution consisting of 25.6 g (0.160 mol) of 1-naphthaldehyde, 29.4 g (0.165 mol) of 2-acetoxyacetophenone, and 300 mL of isopropyl alcohol under cooling with water, and subsequently, the temperature was elevated to 60° C. over one hour and further to 78° C. over 3 hours. After cooling the reaction mixture, a precipitate was collected by filtration, washed with water, and then dried. The resulting dark green powder was suspended in methanol, 8.1 g (0.10 mol) of 70% sodium hydrosulfide was added, and the mixture was heated under reflux for one hour. This methanol solution was cooled, black insoluble matters were filtered off, and the filtrate was evaporated to dryness in vacuo.

The residual solid was dissolved in chloroform and washed with water, the chloroform was distilled off in vacuo, and the dried material was recrystallized from acetonitrile to obtain 12.1 g (yield: 28%) of a milky white powder.

The melting point, Rf value of thin layer chromatography, and NMR and mass spectral data of the resulting powder are as follows.

m.p.: 198 to 202° C.
TLC (silica gel, chloroform/ethyl acetate=9/1), Rf=0.41
NMR (CD$_3$OD): δ 7.0 to 8.4 (m)
MS m/z (%): 270 (M+, 100), 241 (3), 166 (4), 139 (10), 135 (9), 127 (7), 120 (3), 116 (5), 89 (20), 77 (4), 63 (7)

From these spectral data, the resulting compound was identified as 2-(1-naphthyl)-4-phenylimidazole represented by the following formula.

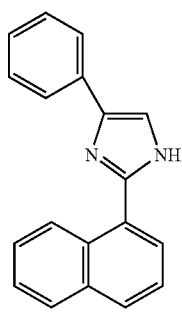

Example 6

Synthesis of 2-(2-naphthyl)-4-phenylimidazole

A solution consisting of 72.4 g (0.363 mol) of copper(II) acetate monohydrate and 230 g (3.38 mol) of 25% ammonia water was added dropwise to a solution consisting of 26.1 g (0.167 mol) of 2-naphthaldehyde, 30.0 g (0.168 mol) of 2-acetoxyacetophenone, and 300 mL of isopropyl alcohol under cooling with water, and subsequently, the temperature was elevated to 60° C. over one hour and further to 78° C. over 3 hours. After cooling the reaction mixture, a precipitate was collected by filtration, washed with water, and then dried. The resulting dark green powder was suspended in methanol, 8.5 g (0.11 mol) of 70% sodium hydrosulfide was added, and the mixture was heated under reflux for one hour. This methanol solution was cooled, black insoluble matters were filtered out, and the filtrate was evaporated to dryness in vacuo. The residual solid was washed with water and dissolved in acetone, oxalic acid was added, and a precipitated oxalate was collected by filtration. This oxalate was suspended in methanol, and sodium methylate was added to liberate a desired material. The methanol was distilled off in vacuo, and the resulting concentrate was washed with water and recrystallized from methanol to obtain 6.1 g (yield: 13.5%) of a pale yellow crystal.

The melting point, Rf value of thin layer chromatography, and NMR and mass spectral data of the resulting crystal are as follows.

m.p.: 194 to 198° C.
TLC (silica gel, chloroform/ethyl acetate=9/1), Rf=0.57
NMR (d$_6$-DMSO): δ 7.22 to 8.48 (m)
MS m/z (%): 270 (M+, 100), 243 (6), 215 (3), 167 (13), 153 (6), 139 (14), 127 (9), 116 (6), 89 (25), 77 (4), 63 (9)

From these spectral data, the resulting compound was identified as 2-(2-naphthyl)-4-phenylimidazole represented by the following formula.

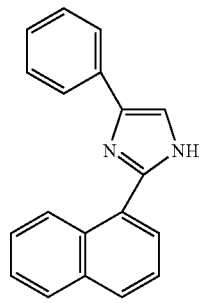

Example 7

Synthesis of 2-(1-naphthyl)-4-phenyl-5-methylimidazole 50.2 g (0.34 mol) of 1-phenyl-1,2-propanedione, 52.9 g (0.34 mol) of 1-naphthaldehyde, and 157 g (2.04 mol) of ammonium acetate were heated under reflux in 250 mL of acetic acid for 3 hours. The reaction mixture was concentrated in vacuo, a large amount of dilute ammonia water was poured into the resulting concentrate, and a precipitated solid was collected by filtration and washed with water. The resulting solid was dissolved in acetone, oxalic acid was added, and a precipitated oxalate was collected by filtration. Next, the collected oxalate was dissolved in methanol, sodium methylate was added to liberate a desired material, and the methanol was distilled off in vacuo. The residual solid was successively washed with water and n-hexane to obtain 30.8 g (yield: 32%) of a milky white crystal.

The melting point, Rf value of thin layer chromatography, and NMR and mass spectral data of the resulting crystal are as follows.

m.p.: 80 to 85° C.
TLC (silica gel, chloroform/ethyl acetate=9/1), R1=0.50
NMR ($d_6$-DMSO): δ 2.53 (s, 3H), 7.14 to 8.02 (m, 12H)
MS m/z (%): 284 (M+, 100), 268 (4), 241 (2), 215 (1), 180 (2), 153 (4), 142 (6), 130 (7), 103 (12), 89 (5), 77 (7), 63 (3)

From these spectral data, the resulting compound was identified as 2-(1-naphthyl)-4-phenyl-5-methylimidazole represented by the following formula.

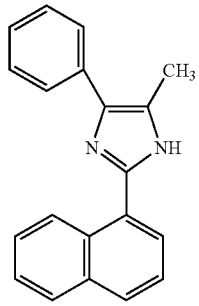

Example 8

Synthesis of
2-(2-naphthyl)-4-phenyl-5-methylimidazole 24.5 g (0.165 mol) of 1-phenyl-1,2-propanedione, 25.8 g (0.165 mol) of 2-naphthaldehyde, and 76.5 g (0.992 mol) of ammonium acetate were heated under reflux in 120 mL of acetic acid for 5 hours. The reaction mixture was concentrated in vacuo, the resulting concentrate was poured into a large amount of dilute ammonia water, and a precipitated solid was collected by filtration and successively washed with water and acetonitrile to obtain 22.7 g (yield: 48.2%) of a pale yellowish brown powder.

The melting point, Rf value of thin layer chromatography, and NMR and mass spectral data of the resulting powder are as follows.

m.p.: 237 to 240° C.
TLC (silica gel, chloroform/ethyl acetate=9/1), Rf=0.57
NMR ($CD_3OD$): δ 2.47 (s, 3H), 7.33 to 8.37 (m, 12H)
MS m/z (%): 284 (M+, 100), 243 (3), 215 (2), 180 (5), 154 (7), 142 (9), 130 (14), 103 (13), 89 (7), 77 (8), 63 (4)

From these spectral data, the resulting compound was identified as 2-(2-naphthyl)-4-phenyl-5-methylimidazole represented by the following formula.

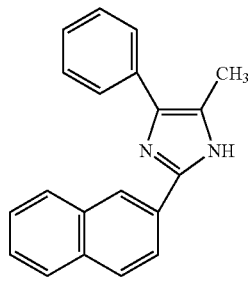

Examples of the surface treating agent using the phenyl-naphthylimidazole compound, the surface treatment method, the soldering method and the printed wiring board according to the invention will be specifically described below with reference to Examples 9 to 22 and Comparative Examples 1 to 7, but it should not be construed that the invention is limited thereto. Incidentally, the soldering test is as follows.

(Evaluation Test for Solder Flow-Up Rate Properties)

A printed wiring board made of a glass epoxy resin of 120 mm (length)×150 mm (width)×1.6 mm (thickness) and having 300 copper through-holes having an inner diameter of 0.80 mm was used as a test piece. This test piece was degreased, subjected to soft etching, and then washed with water. Thereafter, the test piece was dipped in a surface treating agent kept at a prescribed liquid temperature for a prescribed period of time, washed with water, and then dried to form a chemical layer having a thickness of from about 0.10 to 0.50 μm on the copper surface.

The surface-treated test piece was subjected to three cycles of reflow-heating in which the peak temperature was 240° C. using an infrared reflow oven (trade name: MULTI-PRO-306, manufactured by Vetronix Co., Ltd.) and subsequently soldering was performed with a flow soldering device (conveyor speed: 1.0 m/min).

The solder used was a tin-lead eutectic solder with a composition of 63% tin and 37% lead (% by weight) (trade name: H63A, manufactured by Senju Metal Industry Co., Ltd.), and the flux used for soldering was JS-64MSS (manufactured by Koki Co., Ltd.). The soldering temperature was 240° C.

Test piece surface treated as above were also soldered using lead-free solder in the same manner as for the tin-lead eutectic solder. The solder used was lead-free solder (trade name: H705 "ECOSOLDER", manufactured by Senju Metal Industry Co., Ltd.) with a composition of 96.5% tin, 3.0% silver and 0.5% copper (% by weight), and the flux used for soldering was JS-E-09 (manufactured by Koki Co., Ltd.). The reflow-heating peak temperature was 245° C., and the soldering temperature was also 245° C.

For the soldered test piece, the measured result was indicated by the proportion (%) of the number of copper through-holes in which the solder was filled up to the copper land of the copper through-holes with respect to the total number of copper through-holes (300 holes).

When the solder wettability on the copper surface is large, the molten solder penetrates inside each copper through-hole, whereby the molten solder readily fills it to the upper land of the through-hole. More specifically, if the number of through-holes whose upper lands were soldered was large, solder wettability and solderability to the copper would be judged to be excellent.

(Evaluation Test for Solder Spreadability)

A printed wiring board made of a glass epoxy resin of 50 mm (length)×50 mm (width)×1.2 mm (thickness) was used as a test piece. This printed wiring board had a circuit pattern in which 10 pieces of a copper-foiled circuit with a conductor width of 0.80 mm and a length of 20 mm were formed in a width direction at intervals of 1.0 mm. The test piece was degreased, subjected to soft etching, and then washed with water. Thereafter, the test piece was dipped in a surface treating agent kept at a prescribed liquid temperature for a prescribed period of time, washed with water, and then dried to form a chemical conversion film having a thickness of from about 0.10 to 0.50 μm on the copper surface.

The surface-treated test piece was subjected to one cycle of reflow-heating in which the peak temperature was 240° C. using an infrared reflow oven (trade name: MULTI-PRO-306, manufactured by Vetronix Co., Ltd.). Thereafter, a tin-lead solder paste was printed on the center of the copper circuits using a metal mask of 1.2 mm aperture diameter and 150 mm thickness, and reflow-heating was conducted at the above-described conditions for soldering. The tin-lead solder paste used was an eutectic solder (trade name: OZ-63-330E-40-10, manufactured by Senju Metal Industry Co., Ltd.) composed of 63% tin and 37% lead (% by weight).

Test pieces surface treated as above were also soldered using lead-free solder paste in the same manner for the tin-lead solder paste. The lead-free solder used was composed of 96.5% tin, 3.0% silver and 0.5% copper (% by weight) (trade name: M705-221BM5-42-11, manufactured by Senju Metal Industry Co., Ltd.). The peak temperature of reflow-heating attained before and after the solder paste printing was set to 245° C.

The length (mm) of solder which wet and spread over the copper circuit of the obtained test piece was measured.

When the length was longer, solder wettability and solderability would be judged to be excellent.

Example 9

2-Phenyl-4-(2-naphthyl)imidazole as synthesized in Example 2 as a phenylnaphthylimidazole compound and lactic acid and n-heptanoic acid as acids were dissolved in deionized water so as to have a composition as described in Table 1, and the pH was adjusted at 3.2 with ammonia water, thereby preparing a surface treating agent.

Next, a test piece of a printed wiring board was dipped in the surface treating agent as controlled at a temperature of 40° C. for 240 seconds, washed with water, and then dried, thereby measuring the solder flow-up rate properties and solder spreadability. These test results are shown in Table 1.

Examples 10 to 22

Using a phenylnaphthylimidazole compound, an acid, a metal salt and a halogen compound as described in Table 1, surface treating agents having a composition as described in Table 1 were prepared in the same manner as in Example 9 and subjected to a surface treatment under the treatment condition as described in Table 1. With respect to the resulting test pieces, the solder flow-up rate properties and solder spreadability were measured. These test results are shown in Table 1.

Incidentally, 2-(2-methoxyethoxy)acetic acid as used as the acid is a reagent manufactured by SIGMA-ALDRICH. Also, with respect to 2-[2-(2-ethoxyethoxy)ethoxy]acetic acid and 2-{2-[2-(2-ethoxyethoxy)ethoxy]ethoxy}acetic acid, ones synthesized according to the synthesis method as described in *Yukagaku*, Vol. 32, p. 118 (1983) were used.

Comparative Examples 1 to 7

Using an imidazole compound, an acid, a metal salt and a halogen compound as described in Table 2, surface treating agents having a composition as described in Table 2 were prepared in the same manner as in Example 9 and subjected to a surface treatment under the treatment condition as described in Table 2. With respect to the resulting test pieces, the solder flow-up rate properties and solder spreadability were measured. These test results are shown in Table 2.

Incidentally, the imidazole compounds as used in the Comparative Examples are as follows.
- 2-Undecylimidazole (a trade name: C11Z, manufactured by Shikoku Chemicals Corporation)
- 2-Phenylimidazole (a trade name: 2PZ, manufactured by Shikoku Chemicals Corporation)
- 2-Phenyl-4-methylimidazole (a trade name: 2P4MZ, manufactured by Shikoku Chemicals Corporation)
- 2-Nonylbenzimidazole (a reagent, manufactured by SIGMA-ALDRICH)
- 2-(4-Chlorophenylmethyl)benzimidazole (synthesized according to the method as described in *Science of Synthesis*, Vol. 12, 529 (2002))

TABLE 1

| Composition of surface treating agent (% by weight) | Example 9 | Example 10 | Example 11 | Example 12 | Example 13 | Example 14 | Example 15 |
|---|---|---|---|---|---|---|---|
| Imidazole: | | | | | | | |
| 2-Phenyl-4-(1-naphthyl)imidazole (Example 1) | | | 0.25 | | | | |
| 2-Phenyl-4-(2-naphthyl)imidazole (Example 2) | 0.20 | | | 0.20 | | | |
| 2-Phenyl-4-(1-naphthyl)-5-methylimidazole (Example 3) | | | | | 0.25 | | |
| 2-Phenyl-4-(2-naphthyl)-5-methylimidazole (Example 4) | | 0.25 | | | | 0.25 | |
| 2-(1-Naphthyl)-4-phenylimidazole (Example 5) | | | | | | | 0.25 |
| 2-(2-Naphthyl)-4-phenylimidazole (Example 6) | | | | | | | |
| 2-(1-Naphthyl)-4-phenyl-5-methylimidazole (Example 7) | | | | | | | |
| 2-(2-Naphthyl)-4-phenyl-5-methylimidazole (Example 8) | | | | | | | |
| Acid: | | | | | | | |
| Formic acid | | | | | | 15 | 0.5 |
| Acetic acid | | | 10 | | | | 10 |
| Lactic acid | 10 | 10 | | | | 10 | |
| Glycolic acid | | | | | | | |
| Levulinic acid | | | | | 15 | | |
| 2-(2-Methoxyethoxy)acetic acid | | | | | | | |
| 2-[2-(2-Ethoxyethoxy)ethoxy]acetic acid | | | | | | | |
| 2-{2-[2-(2-Ethoxyethoxy)ethoxy]ethoxy}acetic acid | | | | | | | |
| n-Heptanoic acid | 0.10 | | | 0.10 | 0.15 | | 0.10 |
| Metal salt: | | | | | | | |
| Copper acetate | | | | | | 0.20 | 0.10 |
| Cuprous chloride | | | | | | | |
| Cuprous bromide | | | | | | | |
| Cupric chloride | | | | | | 0.08 | |

TABLE 1-continued

| | | | | | | | | |
|---|---|---|---|---|---|---|---|---|
| Cupric bromide | | | 0.10 | 0.10 | | | 0.10 | |
| Zinc acetate | | | | | 0.40 | | | |
| Zinc chloride | | | | | | | | |
| Halogen: | | | | | | | | |
| Ammonium chloride | | | | | | | | 0.10 |
| Potassium chloride | | | | | | | | |
| Ammonium bromide | | | | | | | | |
| Potassium bromide | | | | | | | | |
| Ammonium iodide | | | | 0.07 | | | | |
| Potassium iodide | | | | | 0.05 | 0.08 | | |
| Copper iodide | | | | | | | 0.09 | |
| PH | | 3.2 | 3.1 | 3.0 | 3.3 | 2.3 | 3.0 | 3.1 |
| Treatment condition: | | | | | | | | |
| Treatment temperature (° C.) | | 40 | 50 | 40 | 40 | 50 | 50 | 40 |
| Treatment time (sec) | | 240 | 90 | 120 | 180 | 40 | 90 | 60 |
| Evaluation test: | | | | | | | | |
| Solder flow-up rate properties (%) | Tin-lead based eutectic solder (240° C.) | 100 | 100 | 100 | 98 | 100 | 100 | 100 |
| | Lead-free solder (245° C.) | 94 | 96 | 98 | 100 | 98 | 100 | 95 |
| Solder spreadability (mm) | Tin-lead based eutectic solder (240° C.) | 3.41 | 3.55 | 3.55 | 3.92 | 3.72 | 3.69 | 3.56 |
| | Lead-free solder (245° C.) | 1.62 | 1.61 | 1.63 | 1.65 | 1.63 | 1.68 | 1.66 |

| | Example | | | | | | |
|---|---|---|---|---|---|---|---|
| Composition of surface treating agent (% by weight) | 16 | 17 | 18 | 19 | 20 | 21 | 22 |
| Imidazole: | | | | | | | |
| 2-Phenyl-4-(1-naphthyl)imidazole (Example 1) | | | | | | | |
| 2-Phenyl-4-(2-naphthyl)imidazole (Example 2) | | | | | 0.20 | | |
| 2-Phenyl-4-(1-naphthyl)-5-methylimidazole (Example 3) | | | | | | | |
| 2-Phenyl-4-(2-naphthyl)-5-methylimidazole (Example 4) | | | | | | 0.25 | |
| 2-(1-Naphthyl)-4-phenylimidazole (Example 5) | | | | | | | 0.25 |
| 2-(2-Naphthyl)-4-phenylimidazole (Example 6) | 0.25 | | | | | | |
| 2-(1-Naphthyl)-4-phenyl-5-methylimidazole (Example 7) | | 0.25 | | | | | 0.25 |
| 2-(2-Naphthyl)-4-phenyl-5-methylimidazole (Example 8) | | | 0.15 | | | | |
| Acid: | | | | | | | |
| Formic acid | 10 | 0.5 | | | | | |
| Acetic acid | | | | | | | |
| Lactic acid | | 10 | | | | | |
| Glycolic acid | | | 10 | | | | |
| Levulinic acid | | | | | | | |
| 2-(2-Methoxyethoxy)acetic acid | | | | 5 | 4 | | |
| 2-[2-(2-Ethoxyethoxy)ethoxy]acetic acid | | | | | | 5 | |
| 2-{2-[2-(2-Ethoxyethoxy)ethoxy]ethoxy}acetic acid | | | | | | | 3 |
| n-Heptanoic acid | | 0.10 | | 0.10 | | | 0.10 |
| Metal salt: | | | | | | | |
| Copper acetate | | | | | | 0.10 | |
| Cuprous chloride | | 0.05 | | | | | 0.05 |
| Cuprous bromide | | | 0.07 | | | | |
| Cupric chloride | 0.08 | | | | | | |
| Cupric bromide | | | | | 0.10 | | |
| Zinc acetate | | | | | | | |
| Zinc chloride | | | | 0.20 | | | |
| Halogen: | | | | | | | |
| Ammonium chloride | | | | | | 0.10 | |
| Potassium chloride | | 0.15 | | | | | 0.15 |
| Ammonium bromide | 0.08 | | | | | | |
| Potassium bromide | | | 0.09 | | | | |
| Ammonium iodide | | | | | | | |
| Potassium iodide | | | | | | | |
| Copper iodide | | | | | | | |
| pH | 2.4 | 3.2 | 2.7 | 2.3 | 2.5 | 2.4 | 2.4 |
| Treatment condition: | | | | | | | |
| Treatment temperature (° C.) | 50 | 50 | 50 | 40 | 50 | 50 | 50 |
| Treatment time (sec) | 120 | 25 | 120 | 120 | 60 | 30 | 10 |
| Evaluation test: | | | | | | | |
| Solder flow-up rate properties (%) — Tin-lead based eutectic solder (240° C.) | 100 | 100 | 100 | 100 | 100 | 100 | 100 |
| Lead-free solder (245° C.) | 97 | 96 | 95 | 94 | 95 | 95 | 97 |
| Solder spreadability (mm) — Tin-lead based eutectic solder (240° C.) | 3.61 | 3.77 | 3.65 | 3.44 | 3.62 | 3.72 | 3.89 |
| Lead-free solder (245° C.) | 1.59 | 1.64 | 1.60 | 1.65 | 1.66 | 1.69 | 1.69 |

TABLE 2

| Composition of surface treating agent (% by weight) | Comparative Example | | | | | | |
|---|---|---|---|---|---|---|---|
| | 1 | 2 | 3 | 4 | 5 | 6 | 7 |
| Imidazole: | | | | | | | |
| 2-Undecylimidazole | | | 1.0 | | | | |
| 2-Phenylimidazole | 1.0 | | | 1.0 | | | |
| 2-Phenyl-4-methylimidazole | | | | | 1.0 | | |
| 2-Nonylbenzimidazole | | | | | | 0.20 | |
| 2-(4-Chlorophenylmethyl)benzimidazole | | 0.50 | | | | | 0.50 |
| Acid: | | | | | | | |
| Formic acid | | 3.0 | | | | | 3.0 |
| Acetic acid | 2.0 | | 1.6 | 2.0 | 2.0 | 5.0 | |
| Lactic acid | | | | | | | |
| Glycolic acid | | | | | | | |
| Levulinic acid | | | | | | | |
| 2-(2-Methoxyethoxy)acetic acid | | | | | | | |
| 2-[2-(2-Ethoxyethoxy)ethoxy]acetic acid | | | | | | | |
| 2-{2-[2-(2-Ethoxyethoxy)ethoxy]ethoxy}acetic acid | | | | | | | |
| n-Heptanoic acid | | | | | | | 0.04 |
| Metal salt: | | | | | | | |
| Copper acetate | | 0.20 | 0.10 | | | | 0.10 |
| Cuprous chloride | | | | | | | |
| Cuprous bromide | | | | | | | |
| Cupric chloride | | | | | 0.08 | | |
| Cupric bromide | | | | 0.10 | | 0.10 | |
| Zinc acetate | | | | | | | |
| Zinc chloride | | | | | | | |
| Halogen: | | | | | | | |
| Ammonium chloride | | 0.05 | | | | | |
| Potassium chloride | | | | | 0.07 | | |
| Ammonium bromide | | | | 0.04 | | | 0.04 |
| Potassium bromide | | | | | | 0.05 | |
| Ammonium iodide | | | | | | | |
| Potassium iodide | | | | | | | |
| Copper iodide | | | | | | | |
| PH | 6.2 | 2.7 | 4.4 | 6.2 | 6 | 2.9 | 2.6 |
| Treatment condition: | | | | | | | |
| Treatment temperature (° C.) | 50 | 40 | 50 | 50 | 50 | 40 | 50 |
| Treatment time (sec) | 240 | 180 | 25 | 120 | 40 | 30 | 60 |
| Evaluation test: | | | | | | | |
| Solder flow-up rate properties (%) — Tin-lead based eutectic solder (240° C.) | 32 | 71 | 8 | 36 | 41 | 80 | 82 |
| Solder flow-up rate properties (%) — Lead-free solder (245° C.) | 14 | 44 | 0 | 12 | 15 | 45 | 47 |
| Solder spreadability (mm) — Tin-lead based eutectic solder (240° C.) | 2.21 | 2.40 | 2.12 | 2.41 | 2.44 | 2.38 | 2.41 |
| Solder spreadability (mm) — Lead-free solder (245° C.) | 1.42 | 1.41 | 1.38 | 1.41 | 1.41 | 1.43 | 1.44 |

According to the test results as shown in Table 1 and Table 2, it is submitted that in the case where the surface treating agent according to the invention is brought into contact with the surface of copper to form a chemical layer, which is then subjected to soldering using an eutectic solder or a lead-free solder, the solder wettability is greatly improved in both eutectic soldering and lead-free soldering because the solder flow-up rate properties and solder spreadability are remarkably enhanced.

This disclosure is based upon, and claims priority from, Japan patent application No. 2004-173150 filed on Jun. 10, 2004, Japan patent application No. 2004-218230 filed on Jul. 27, 2004, and Japan patent application No. 2005-128938 filed on Apr. 27, 2005, the contents of which are incorporated by reference herein.

The invention claimed is:

1. A phenylnaphthylimidazole compound selected from the group consisting of 2-phenyl-4-(1-naphthyl)-5-methylimidazole and 2-phenyl-4-(2-naphthyl)-5-methylimidazole.

2. A surface treating agent for copper or a copper alloy, which comprises a carrier and a phenylnaphthylimidazole compound selected from the group consisting of 2 phenyl-4-(1-naphthyl)-5-methylimidazole and 2-phenyl-4-(2-naphthyl)-5-methylimidazole.

3. The surface treating agent for copper or a copper alloy of claim 2, which comprises the carrier and the phenylnaphthylimidazole compound in a proportion of from 0.01 to 10% by weight.

4. The surface treating agent for copper or a copper alloy of claim 2, comprising the phenylnaphthylimidazole compound in a proportion of from 0.01 to 10% by weight and an organic acid or an inorganic acid in a proportion of from 0.1 to 50% by weight, wherein the surface treating agent is an aqueous solution.

5. The surface treating agent of claim 2, wherein the carrier is water or an organic solvent.

6. A surface treating agent for copper or a copper alloy, which comprises a carrier and a phenylnaphthylimidazole compound represented by the following formula (I):

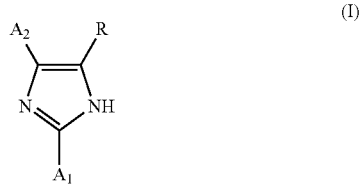

wherein $A_1$ is a phenyl group; $A_2$ represents a 1-naphthyl group or a 2-naphthyl group; and R represents a hydrogen atom or a methyl group, further comprising a copper compound or a zinc compound.

7. The surface treating agent of claim 6, wherein the copper compound is present in a proportion of from 0.01 to 10% by weight.

8. The surface treating agent of claim 2, further comprising a halogen compound.

9. The surface treating agent of claim 8, wherein the halogen compound is selected from the group consisting of sodium fluoride, potassium fluoride, ammonium fluoride, sodium chloride, potassium chloride, ammonium chloride, sodium bromide, potassium bromide, ammonium bromide, sodium iodide, potassium iodide, and ammonium iodide.

10. The surface treating agent of claim 8, wherein the halogen compound is present in a proportion of from 0.001 to 1% by weight.

11. A surface treatment method for copper or a copper alloy, which comprises bringing the surface of copper or a copper alloy into contact with the surface treating agent according to any one of claims 2 to 4.

12. A printed wiring board, which comprises copper or a copper alloy constituting a copper circuit part, wherein the surface of copper or the alloy has been brought into contact with the surface treating agent according to any one of claims 2 to 4.

13. A soldering method, which comprises bringing the surface of copper or a copper alloy into contact with the surface treating agent according to any one of claims 2 to 4 and then performing soldering.

14. The surface treating agent of claim 6, wherein the copper compound is selected from the group consisting of copper acetate, cuprous chloride, cupric chloride, cuprous bromide, cupric bromide, copper iodide, copper hydroxide, copper phosphate, copper sulfate, and copper nitrate.

15. The surface treating agent of claim 6, wherein the zinc compound is selected from the group consisting of zinc oxide, zinc formate, zinc acetate, zinc oxalate, zinc lactate, zinc citrate, zinc sulfate, zinc nitrate, and zinc phosphate.

* * * * *